(12) United States Patent
Reidelberger

(10) Patent No.: US 8,977,517 B2
(45) Date of Patent: Mar. 10, 2015

(54) SYSTEM AND METHODS FOR EVALUATING EFFICACY OF APPETITE-AFFECTING DRUGS

(75) Inventor: Roger D. Reidelberger, Omaha, NE (US)

(73) Assignee: Creighton University, Omaha, NE (US)

( * ) Notice: Subject to any disclaimer, the term of this patent is extended or adjusted under 35 U.S.C. 154(b) by 1885 days.

(21) Appl. No.: 11/809,948

(22) Filed: Jun. 4, 2007

(65) Prior Publication Data

US 2007/0280887 A1   Dec. 6, 2007

Related U.S. Application Data

(60) Provisional application No. 60/811,040, filed on Jun. 5, 2006.

(51) Int. Cl.
*A01K 1/00* (2006.01)
*A61K 49/00* (2006.01)
*G01N 33/50* (2006.01)

(52) U.S. Cl.
CPC ........ *A61K 49/0008* (2013.01); *G01N 33/5088* (2013.01)
USPC ............................ 702/179; 119/340; 119/417

(58) Field of Classification Search
None
See application file for complete search history.

(56) References Cited

U.S. PATENT DOCUMENTS

| | | | |
|---|---|---|---|
| 3,897,751 A | 8/1975 | Gullino | |
| 4,457,750 A | 7/1984 | Hill | |
| 4,709,331 A | 11/1987 | Barkett | |
| 4,756,707 A | 7/1988 | MacLeod | |
| 4,807,170 A | 2/1989 | Kulli | |
| 4,900,313 A | 2/1990 | MacLeod | |
| 5,008,821 A | 4/1991 | Pratt et al. | |
| 5,100,380 A | 3/1992 | Epstein | |
| 5,163,380 A | 11/1992 | Duffy | |
| 5,429,602 A | 7/1995 | Hauser | |
| 5,560,317 A | 10/1996 | Bunyan | |
| 5,593,390 A | 1/1997 | Castellano | |
| 5,609,575 A | 3/1997 | Larson | |
| 5,681,285 A | 10/1997 | Ford | |
| 5,685,844 A | 11/1997 | Marttila | |
| 5,772,635 A | 6/1998 | Dastur | |
| 5,816,256 A | 10/1998 | Kissinger | |
| 5,832,878 A | 11/1998 | Bonsall | |
| 5,865,766 A | 2/1999 | Bonsall | |
| 5,925,021 A | 7/1999 | Castellano | |
| 6,044,795 A | 4/2000 | Matsuura | |
| 6,062,224 A | 5/2000 | Kissinger | |
| RE36,871 E | 9/2000 | Epstein | |
| 6,234,111 B1 | 5/2001 | Ulman | |
| 6,269,340 B1 | 7/2001 | Ford | |
| 6,279,511 B1 | 8/2001 | Loughnane | |
| 6,367,418 B1 | 4/2002 | Ulman | |
| 6,468,242 B1 | 10/2002 | Wilson | |
| 6,497,197 B1 | 12/2002 | Huisma | |
| 6,516,749 B1 | 2/2003 | Salasidis | |
| 6,542,850 B2 * | 4/2003 | Ulman et al. | 702/179 |
| 6,554,822 B1 | 4/2003 | Holschneider | |
| 6,681,717 B2 | 1/2004 | Burghardi | |
| 6,748,898 B2 | 6/2004 | Ulman | |
| 6,863,023 B2 | 3/2005 | Burghardi | |
| 6,868,804 B1 | 3/2005 | Huisma | |
| 6,886,493 B1 | 5/2005 | Deneintolis | |
| 7,459,432 B2 * | 12/2008 | Cowley et al. | 514/1.1 |
| 2003/0163112 A1 | 8/2003 | Makkink | |
| 2004/0006280 A1 | 1/2004 | Geddes | |
| 2004/0054320 A1 | 3/2004 | Kissinger | |
| 2005/0066910 A1 | 3/2005 | Tecott | |
| 2005/0277912 A1 * | 12/2005 | John | 604/890.1 |
| 2007/0083090 A1 * | 4/2007 | Sterling et al. | 600/300 |
| 2009/0126640 A1 * | 5/2009 | Ulman et al. | 119/54 |

OTHER PUBLICATIONS

Columbus Instruments; Feeding Computer: Feed Scale http://colinst.com/brief.php?id=33.
Research Diets, Inc; BioDAQ Food Intake Monitor http://www.researchdiets.com/biodaq/index.htm.

* cited by examiner

*Primary Examiner* — Anna Skibinsky
(74) *Attorney, Agent, or Firm* — Advent, LLP

(57) ABSTRACT

System and methods to evaluate and administer drugs. The present invention instantaneously identifies the effects that drugs, including appetite-affecting agents, have on animals. Data is collected automatically and analyzed and further organized to identify feeding patterns and the effect an appetite-affecting agent has on those feeding patterns. The present invention includes a system for data management, including a program with a data acquisition phase and a data analyzing phase to determine the feeding patterns of animals to aid in the evaluation of appetite-affecting drug efficacy.

11 Claims, 5 Drawing Sheets

SYSTEM AND METHODS FOR EVALUATING EFFICACY OF APPETITE-AFFECTING DRUGS

This application claims the benefit of U.S. Provisional Application No. 60/811,040 filed Jun. 5, 2006.

FIELD OF THE INVENTION

The present invention relates to a system and methods for evaluating the efficacy of drugs, or agents. More particularly, the present invention relates to a system and methods by which data can be managed, such as collected analyzed and organized, to determine the effect that a particular agent may have on appetite, including, for example, feeding patterns and changes thereto.

BACKGROUND OF THE INVENTION

For purposes of this application, the present invention is discussed in reference to efficacy of appetite-affecting drugs, or agents, but the present invention is applicable to any drug for which the efficacy is sought.

Drug efficacy is a constant study conducted in numerous research fields. Particularly, with respect to drug efficacy on appetite, it is desirable to determine whether chronic administration of such drugs, or agents, can produce a sustained decrease in daily food intake.

It has long been known to administer appetite-affecting agents, such as putative anorexigenic or anti-obesity agents, to an animal and then observe the effects, if any, on the animal's feeding pattern, or eating habits. Known methods of administering appetite-affecting agents typically include either daily injections or insertion of an osmotic mini-pump beneath the skin or into the peritoneal cavity to deliver agents continuously for a week or more. In addition, the food provided to the animal is weighed on a regular basis so that daily food intake can be monitored. Typically, these methods are inconclusive due to an increase in food intake between administrations of the agent as well as a developed tolerance to the agent.

After the administration is complete, the animals are evaluated to determine what effect, if any, the appetite-affecting agent had on the animal's eating habits. Typically, such evaluation has been limited to analyzing the animal's daily food intake by weight and dissecting the animal to determine adiposity, which is the amount and type of fat stored in fatty tissue. Conclusions regarding the agent's overall efficacy are based primarily on this evaluation.

Methods for evaluating drug efficacy have problems. For example, animals can experience decreased appetite following administration of appetite-affecting agents, and thus an overall decrease in food intake for a duration of time. It is also known that animals may experience hyperphagia, or excessive hunger leading to an increased food intake. This typically occurs following an anorexic episode that follows a dose of an anti-obesity appetite-affecting agent. Similarly, an animal may develop a tolerance to the appetite-affecting agent if administered in a particular dose over too long a duration of time. Thus, evaluating the efficacy of an administered drug requires an ability to measure the instantaneous effects of different doses including frequency of administration of the drug on feeding patterns.

A specific example related to the above-described problem includes difficulty in adjusting administration of the agent with respect to dosage and frequency to balance hyperphagia against anorexic episodes. Because the data collected by current methods is limited, it is difficult to maximize the efficacy of agents to augment an animal's feeding patterns. Limited data hinders an accurate analysis of feeding patterns as well as the ability to track changes in these patterns. Increasing the number of animals observed cannot alleviate these problems, thus, these problems prevent sufficient data management, including collection and analysis, to optimize the efficacy of appetite-affecting agents.

A demand therefore exists for a system and methods to administer and evaluate drugs. Data is collected and analyzed to determine the effects that a particular agent has on appetite including, for example, identifying feeding patterns and the effect the agent has on those feeding patterns. The present invention satisfies the demand.

SUMMARY OF THE INVENTION

Embodiments of the present invention administer and evaluate drugs. The present invention instantaneously identifies the effects that drugs, including appetite-affecting agents, have on animals. Data is collected, analyzed and organized to identify feeding patterns and the effect the agent has on those feeding patterns. Feeding patterns include, for example, amount, duration and frequency of food intake as distinct meals. A meal is defined as an interval of feeding during which food intake is greater than a predetermined value, the minimum meal size. This interval of feeding must also be preceded and followed by a pause in food intake greater than a predetermined value, the minimum between-meal interval The present invention includes at least one cage and scale assembly, or cage scale assembly, and a drug-delivery device. The cage scale assembly includes a cage and a scale. The cage can be anything that houses the animal being administered with the drug, for example, a box, corral, crate, enclosure, or pen, to name a few. The cage houses an animal, which is any multicellular organism, such as a human, monkey, or rat, such as a Sprague-Dawley rat. The scale measures the weight or mass of an object, and is preferably electronic, although it is contemplated the scale could be a beam scale, balance scale, spring scale, or even a hydraulic or pneumatic scale.

The scale measures the weight or mass of a food source available to the animal. The term "food source" for purposes of this application means any substance, usually composed primarily of carbohydrates, fats, water and/or proteins, that can be eaten or drunk by an animal for nutrition and/or pleasure, including solid block food, pellet food, liquid food, to name a few.

The drug-delivery device includes a pump and a drug source. The pump administers the drug from the drug source to the animal. The pump can be any apparatus that delivers, or moves, liquids, for example, a positive displacement pump, a centrifugal pump, or a kinetic pump.

The drug source houses the drug, or appetite-affecting agent, to be administered to the animal. The drug source can be a syringe, piston apparatus, vial, bag, bottle, beaker, or flask, to name a few. The appetite-affecting agent, for purposes of this application, is any drug or agent whose effect, if any, on appetite is being studied and may include a placebo used in such study. Examples of such appetite-affecting agents include, for example, peptides, such as Peptide $YY_{3-36}$ (PYY), cholecystokinin, amylin, salmon calcitonin, glucagon-like peptide-1 (GLP-1), exendin-4, oxyntomodulin, pancreatic polypeptide, gastrin-releasing peptides GRP-27 and GRP-10, enterostatin, apolipoprotein A-IV, leptin, melanocortin receptor 3 and 4 agonists including melanotan II, opioid receptor antagonists including naloxone and naltrexone, and endocanabinoid receptor antagonists AM251 and Rimonabant, to name a few.

It is contemplated that one pump can control a plurality of drug sources, although the drug sources need not be grouped and each individual drug source may instead be associated with its own individual, dedicated pump.

The pump administers, or delivers, the appetite-affecting agent from the drug source to the animal via an infusion line. A swivel-tether connector is positioned within the infusion line to allow the animal to move freely. The animal is attached to the infusion line by a catheter surgically implanted, for example, in its jugular vein, peritoneal cavity, or under the skin. The animal wears a jacket that includes a harness to keep the catheter and infusion line intact during and subsequent to administration of the appetite-affecting agent.

A switchbox controls one or more cage scale assemblies. The switchbox allows data to be received from each cage scale assembly either sequentially, or randomly, switching between the plurality of cage scale assemblies.

After the switchbox receives data from each cage scale assembly, the data is sent to a control unit, such as a computer. The control unit communicates with the cage scale assembly, drug-delivery device, or both. The control unit can communicate the operation of the pump to administer the appetite-affecting agent. The control unit can be pre-programmed with a particular sequence of operation or can determine the administration of the appetite-affecting agent based on the data received from the cage scale assembly.

The control unit can communicate with the cage scale assembly, drug-delivery device, or both, via a network. The network can include, for example, Integrated Services Digital Network (ISDN), Digital Subscriber Line (DSL), Fiber Optic Network, Satellite Networks (SN), Wireless Wide Area Networks (WWAN), Recommended Standard 232 (RS232) Computer Serial Interface Networks, and Universal Serial Bus (USB) Networks, to name a few.

It is also contemplated that embodiments of the present invention may include a plurality of control units. For example, a first computer may be configured to communicate with the drug-delivery device, and a second computer configured to communicate with the scale. Each of these computers, in turn, may be configured to communicate with a third computer, for example to receive instructions regarding operation of the system. Each of the computers may be further configured to communicate with each other over a network, as discussed above, or by being directly connected to one another. Other embodiments may consolidate the functions of the first and second computers into a single computer that is configured to communicate with the drug-delivery device and the scale, and which may be further configured to communicate with and be controlled by the third computer.

The control unit is configured to manage data received from the switchbox of the cage scale assembly. The data is collected into a database and analyzed. The data, or database, can further be organized into records. The data includes animal identification number, date, time, and value of food weight, amount of food intake during specified intervals of time, time of occurrence, duration, size and frequency of distinct meals, and average meal size, meal duration and number of meals during specified intervals of time.

The control unit can also be configured to manage data sent to and received from the drug-delivery device, such as animal identification number, date of drug delivery, type of appetite-affecting agent delivered, location of drug delivery, dose and volume infusion rate.

The data determines the efficacy of the drug. For example, the present invention determines the effect of a particular dose, frequency and location of administration of an appetite-affecting agent on feeding patterns and amount of food intake.

The present invention includes a system for data management, including data collection, analysis and further organization into data records. According to the present invention, the data management system includes a program with a data acquisition phase and a data analyzing phase. Data is collected during the data acquisition phase. As discussed above, data includes animal identification number, date, time, and value of food weight, date and time of agent delivery, type of appetite-affecting agent delivered to the animal, location of agent delivery, dose and volume infusion rate.

The data acquisition phase includes an initial setup segment and a data collection segment. The initial setup segment can be entered via a graphical user interface on a control unit, or computer, implementing the program. The initial setup segment facilitates the input of the parameters for evaluating the efficacy of drugs. The parameters include control parameters and information parameters regarding overall variables, such as study identification, date, animal environment lights on/off times, and start/stop times. The initial setup segment may also allow input of control parameters and information parameters pertaining to each animal, for example, an animal's identification number, corresponding scale identification number, and treatment information, such as agent and dose. The initial setup segment also includes pump setup for the input of control parameters and information parameters that may include pump identification number corresponding to a particular animal, the syringe diameter, infusion rate, and infusion periods. Additional inputs may include control parameters and information parameters regarding the periodicity of the retrieval of data from the scales associated with the food source of each animal, such as the interval at which data will be collected from each scale, and the control parameters defining the feeding of an animal. Such feedings typically include a change of weight of the food source from one data interval to the next that exceeds a predetermined threshold value.

At a predetermined time, the program starts and switches "on" the pump of the pump assembly. The appetite-affecting agent is delivered to the animal according to the parameters input during the initial setup segment. The first scale is polled to collect data associated with a first cage and a first animal. The program compares the current value of the food weight to the previously polled food weight from the same scale, to determine whether the absolute change in food weight exceeds a predetermined threshold value indicative of feeding behavior. If the change in value is greater than the predetermined threshold value, the data is recorded for later analysis. If the change in value is less than the predetermined threshold value, no data is recorded. The switchbox instructs the system to switch to the next cage, or second cage, to poll the second scale weight.

The data analyzing phase analyzes the data collected into a database. The data analyzing segment includes a program setup, which may include, for example, data records to analyze, the animal identification data to analyze, and the meal criteria. Defining meal criteria may include defining the minimum meal size in terms of change in food weight, and defining the minimum between-meal interval. The minimum between-meal interval is defined as a predetermined time period of no eating that must be met to define the end of one meal and the start of another.

The data analyzing program imports the stored data. The data records preferably contain information necessary to determine feeding patterns in the animals being studied, such as animal identification numbers, the time and date the data were collected, food weight from previous data acquisition, and food weight from current data acquisition. The program then sorts the data into records. The data records may be sorted by date, animal identification number, and/or the time that the data was recorded. Other sorting may also be performed according to predefined criteria, such as the user's preferences.

Once the program has sorted the data into records, for example, by date, animal identification number, and time of recording, it may determine feeding patterns during specific intervals of time for each animal according to predetermined parameters. Examples of feeding patterns may include identifying the time of occurrence, duration, size and frequency of distinct meals. A meal is defined as an interval of successive food weight data for a specified animal showing a beginning to end difference in food weight that is greater than a predetermined value, the minimum meal size. This interval of successive food weight data must also be preceded and followed by a pause in food weight recording greater than a predetermined value, the minimum between-meal interval. Additional feeding pattern data may include meal start time, meal duration (defined as the absolute value of meal start time minus meal end time for a particular animal), and post-meal interval (preferably defined as the absolute value of meal start time plus meal duration minus next meal start time for a particular animal), and average meal size, meal durations and number of meals during specified intervals of time. After one or more feeding patterns have been identified, the program preferably saves the data.

Once one or more feeding patterns have been identified, the program may perform the step of displaying the feeding pattern data on, for example, a graphical user interface using graphics and/or text. Displaying the feeding pattern data in graphics and/or text allows instantaneous identification of data trends as well as an instantaneous visualization of the effects of the agent on an animal's feeding patterns, or on average feeding patterns from a group of identically treated animals.

An object of the present invention is to optimize the determination of the efficacy of drugs.

Another object of the present invention is to allow precise administration of drugs, or agents, to animals.

Another object of the present invention is to instantaneously identify the effects that drugs, including appetite-affecting agents, have on animals.

Another object of the present invention is to resolve the intense debate regarding the inhibitory effects of appetite-affecting drugs on food intake and body weight.

Another object of the present invention is to determine the efficacy of oral and/or intragastric administration of appetite-affecting agents.

An object of the present invention is to identify substances that can sustain a reduction in daily food intake and body fat in obese animals, and sustain an increase in daily food intake and body fat in excessively lean animals.

Another object of the present invention is to minimize known obstacles to optimizing efficacy for appetite-affecting drugs, for example hyperphagia between intervals of infusion and the development of tolerance to such drugs.

Another object of the present invention is to allow an animal free access to food sources such that an animal's consumption of the food source is not restricted.

Another object of the present invention is to determine feeding patterns associated with appetite-affecting agents for the treatment of obesity and excessive leanness.

Yet another object of the present invention is to manage, collect and analyze data to identify feeding patterns.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which.

DETAILED DESCRIPTION

The present invention relates to a system and methods for evaluating the efficacy of drugs, or agents. For purposes of this application, the present invention is discussed in reference to efficacy of appetite-affecting drugs, or agents, but the present invention is applicable to any drug for which the efficacy is sought. It is contemplated that the present invention is applicable to all types of settings, including research settings, without regard to the animals used or the drugs administered to the animals, and advantageously permits a wide scope of research to be conducted.

Figure 1:
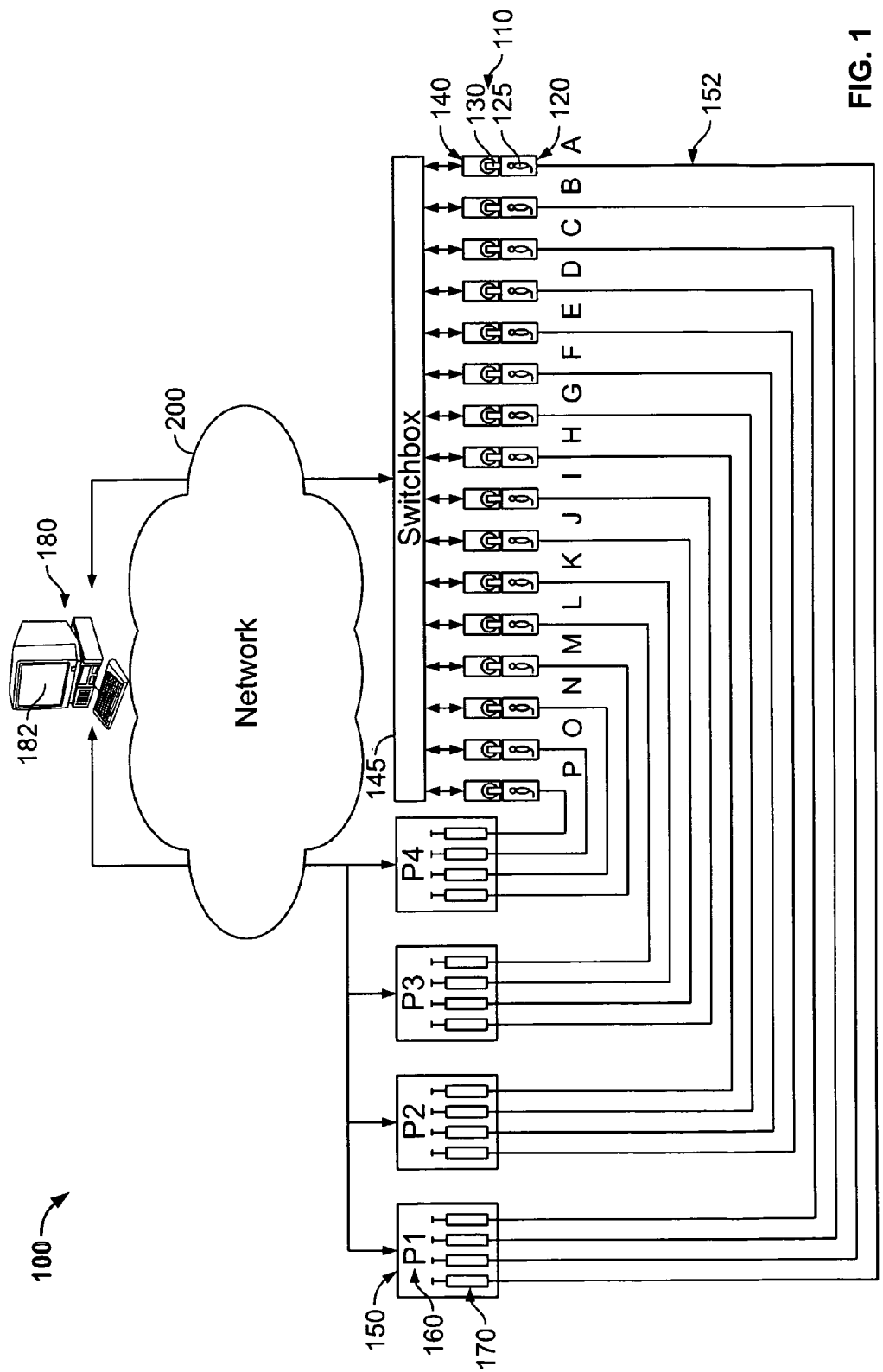
FIG. 1 is a top view of an embodiment of a system to determine drug efficacy according to the present invention.

FIG. 1 shows a schematic for an embodiment of a system 100 for administering and evaluating the efficacy of appetite-affecting agents in a plurality of animals. In particular, the system 100 is configured for the automatic administration of appetite-affecting agents to animals and managing the data from each respective animal. The system 100 includes a plurality of cage and scale assemblies 110, termed also cage scale assemblies 110 for purposes of this application. As described below, one embodiment of such cage scale assembly 110 includes a cage 120, an animal 125 within the cage 120, a food source 130, and a scale 140 associated with the food source 130 that may be configured to communicate over a network 200.

The system 100 of FIG. 1 includes a plurality of drug-delivery device 150, each of which includes a pump 160 and one or more drug sources 170. A fluid from the drug source 170 is delivered to an animal 125 as shown by infusion lines 152A-P in FIG. 1. The cage scale assemblies 110 and drug-delivery device 150, which are described in greater detail below with respect to FIG. 2, may further be configured to communicate with a control unit 180, such as computer 182, over a network 200, for example to receive operating instructions or manage the collected and analyzed data. As shown in the system 100 of FIG. 1, multiple drug sources 170 may be grouped together with the pump 160 of the drug-delivery device 150. Such groupings allow for common control of a plurality of drug sources 170 by one pump 160. The drug sources 170 need not be grouped, however, and each individual drug source 170 may instead be associated with its own individual, dedicated pump 160.

The system 100 may include a control unit 180, such as computer 182, which may be configured to communicate with and operate the drug-delivery device 150. The computer 182 may be configured to receive and analyze data received from the plurality of cage scale assemblies 110. Preferably, each cage scale assembly 110 of a group of cage assemblies 110A-P is operatively connected to a switchbox 145. One embodiment of the switchbox 145 allows data to be received from each cage scale assembly 110 by sequentially, or randomly, switching between the plurality of cage scale assemblies 110A-P. The data received by the switchbox 145 is sent to a control unit 180 having a storage medium for managing the data. It is contemplated that the switchbox 145 may communicate with and be controlled by the control unit 180, here computer 182.

Figure 2:
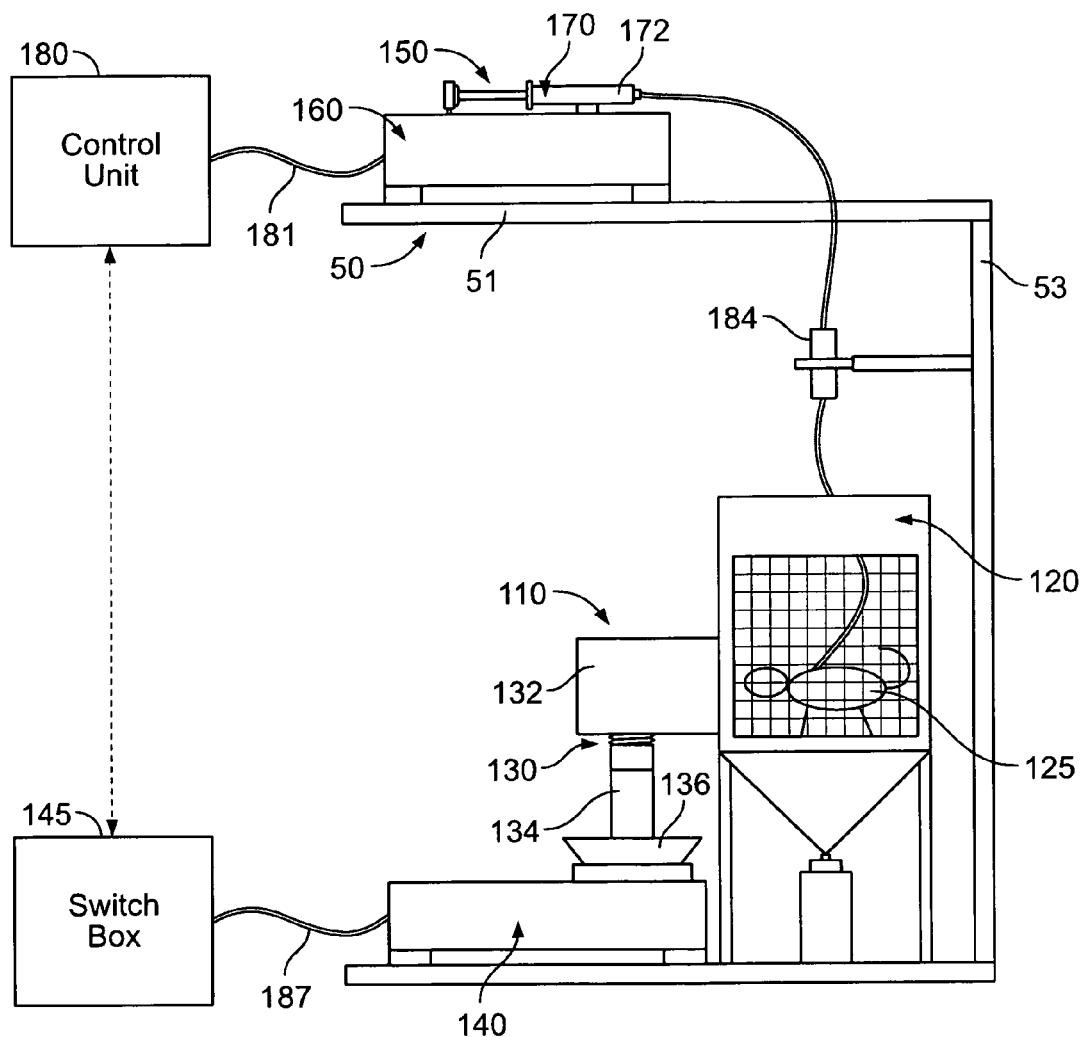
FIG. 2 is a side view of the embodiment of FIG. 1 according to the present invention.

FIG. 2 is a side view of the embodiment of FIG. 1 according to the present invention. The system 100 includes a cage scale assembly 110 and a drug-delivery device 150. In general, the drug-delivery device 150 includes a drug source 170, here a syringe 172 that delivers a quantity of the drug, or fluid. Drug source 170 may be operatively mounted to a pump 160. Pumps 160 are well known in the art, and are controlled by a control unit 180. As shown in FIG. 2, pump 160 is connected to a control unit 180 by cable 181. Pump 160 may also be remotely controlled or actuated for delivery of the fluid at desired times and desired amounts. The pump 160 provides the fluid to an animal 125 from the drug source 170.

Other embodiments may include wireless communication between the pump 160 and control unit 180. The animal 125, such a Sprague-Dawley rat for example, may be connected to the drug source 170 such as through an infusion line 152A that is preferably connected to a catheter implanted in the jugular vein, peritoneal cavity, or under the skin of the animal 125, or any other methods that are well known in the art. A swivel-tether connector 184 between the infusion line 152A allows the animal 125 to move freely about its cage 120. In this embodiment, as shown in FIG. 2, the drug-delivery device 150 may be placed in a supported position such as a shelf 50, with a horizontal member 51 and vertical member 53 near and/or above the cage 120. Of course, the drug source 170 need not be so placed, and can be placed in any convenient location.

The cage scale assembly 110 includes an animal 125 within a cage 120. A food source 130 is available to the animal 125, through a hole (not shown) in the base of a side-compartment 132 attached to the cage 120. The food source 130 may be placed on a stand 134 that sits in a dish 136, which functions to catch falling food that may become dislodged from the food source 130 as the animal 125 engages in eating. The food source 130 is further associated with a scale 140 for measuring the weight of the food source 130. The scale 140 is preferably electronic and may be in communication with the switchbox 145. The switchbox 160 can wirelessly communicate with the cage scale assembly 110 and further with the control unit 180. A shown in FIG. 2, the switchbox 145 communicates with the scale 140 by way of cable 187. The scale 140 may be alternately configured to communicate with and be controlled by the control unit 180, over a network 200 as described in reference to FIG. 1.

Figure 3:
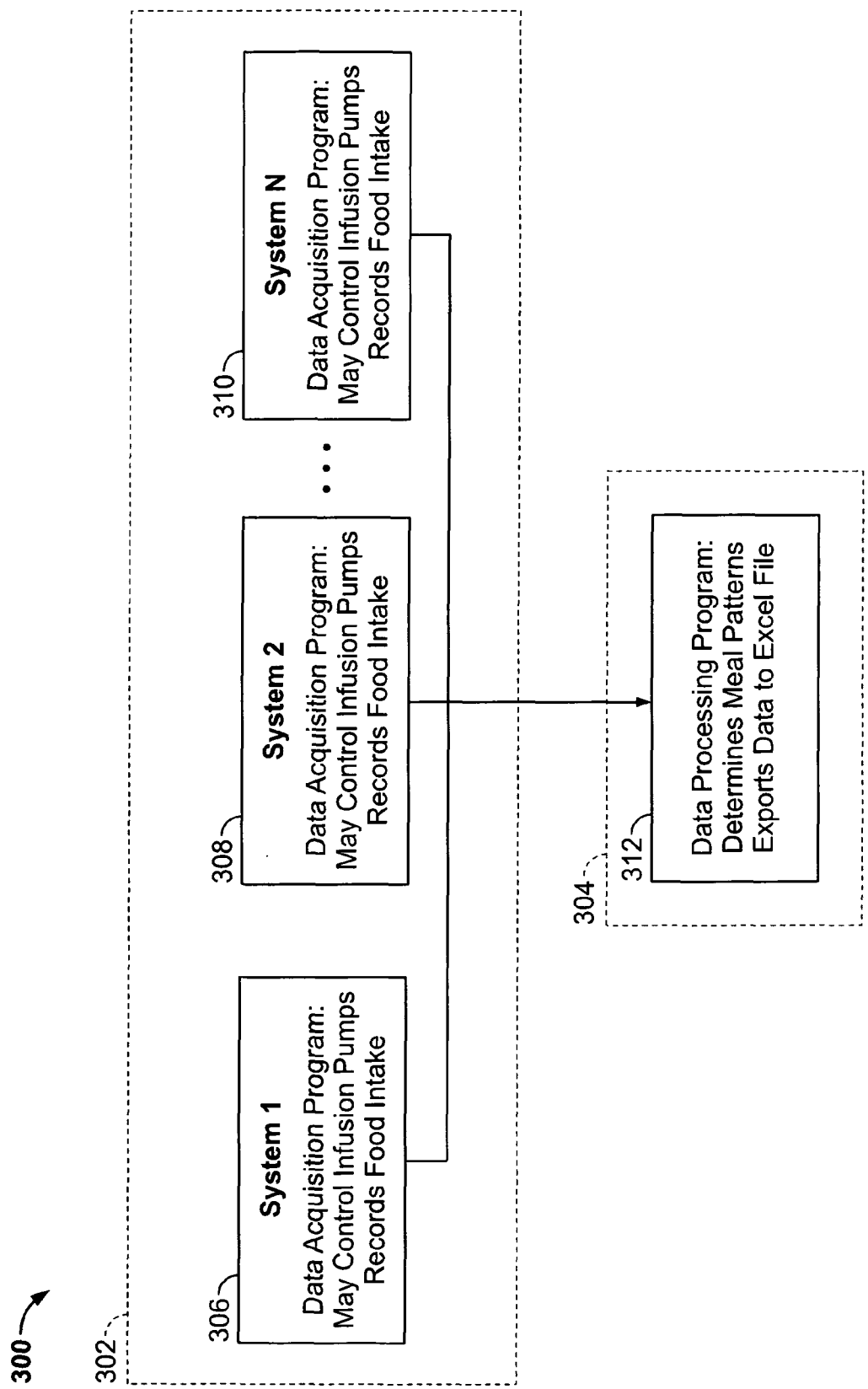
FIG. 3 is a flowchart of an embodiment of a data management system including a data acquisition phase and a data analyzing phase according to the present invention.

The embodiment in FIGS. 1 and 2 includes a system for data management, including data collection and analysis. FIG. 3 is a flowchart of a data management system 300 according to the present invention. The data management system 300 may include two phases, the data acquisition phase 302 and the data analyzing phase 304.

As shown in FIG. 3, the data acquisition phase 302 includes one or more systems 306, 308, 310 that deliver appetite-affecting agents to animals, and further collect data. The desired times and desired amounts of delivery of the appetite-affecting-agents can be dependent upon the data collected. Thus, the data received and analyzed dictates the administration of the appetite-affecting agent.

As explained in greater detail below, data acquisition systems 306, 308, 310 may include a program implemented on a control unit 180, such as the computer 182 shown in FIG. 1. The control unit 180 not only controls the drug-delivery device 150, but also collects data, for example, animal identification number, date, time, and food weight. The overall system 300 is scalable to accommodate any number of animals in one or more locations. As explained in greater detail below, the data analyzing phase 304 may include use of a program 312 that may be implemented on a control unit 180 to use data collected during the data acquisition phase 302 to determine effects of the drug on feeding patterns.

Although the system 100 shown and described with respect to FIGS. 1 and 2 employ only a control unit 180, or computer 182, embodiments of the system 100 may include a plurality of control units 180, or computers 182, to operate the system 100. For example, the system 100 may include a first computer configured to communicate with the drug-delivery device, and a second computer configured to communicate with the scale. Each of these computers, in turn, may be configured to communicate with a third computer, for example to receive instructions regarding operation of the drug-delivery device and food source. Each of the computers may be further configured to communicate with each other over a network, or by being directly connected to one another. Other embodiments may consolidate the functions of the first and second computers into a single computer that is configured to communicate with the drug-delivery device and the scale, and which may be further configured to communicate with and be controlled by the third computer.

Figure 4:
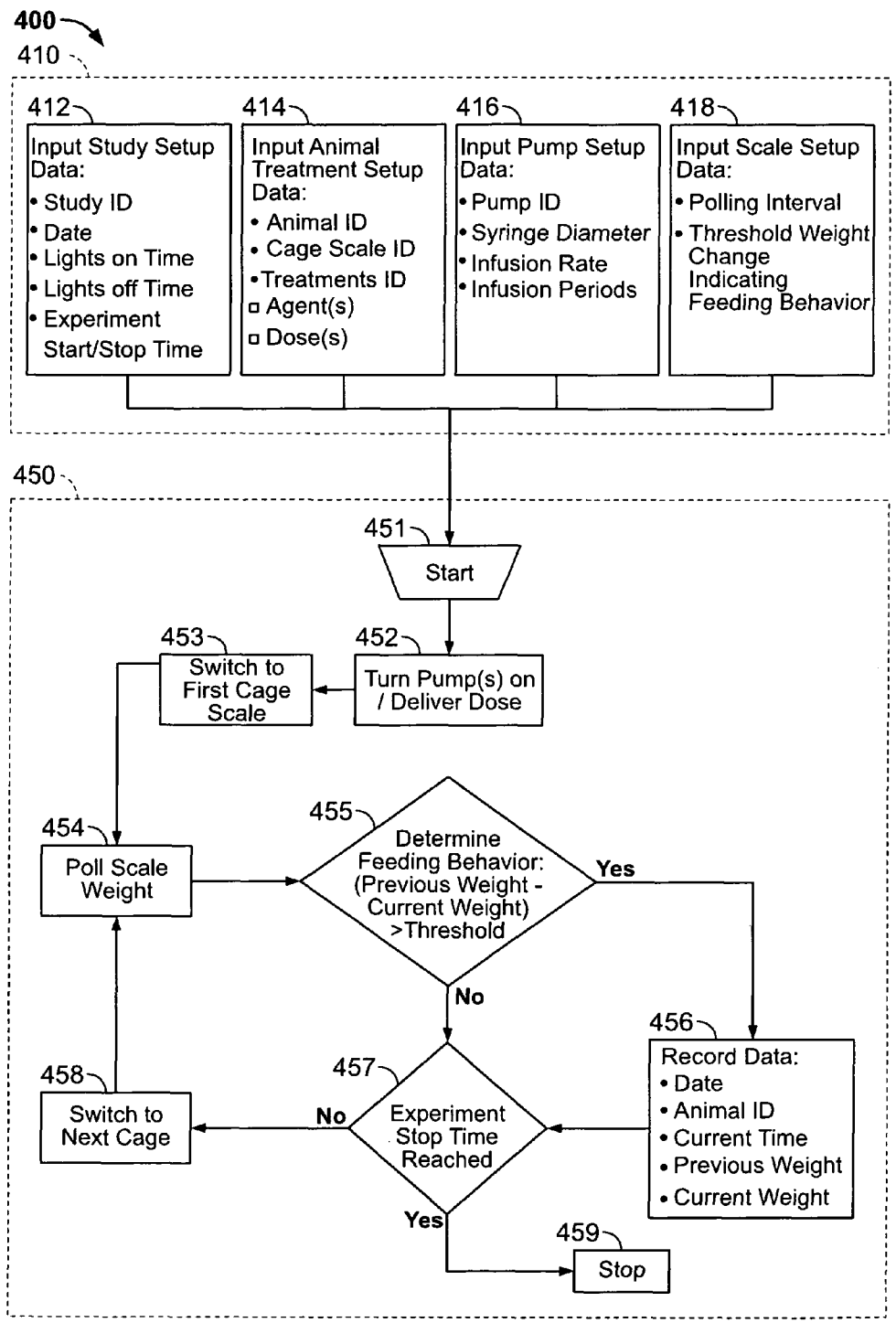
FIG. 4 is a flowchart of an embodiment of the data acquisition phase of FIG. 3 according to the present invention.

Determining animal feeding patterns ideally requires the control and monitoring of a number of factors and conditions. FIG. 4 is a flowchart of an embodiment of the data acquisition phase 302 of the present invention. In one embodiment, a data acquisition program 400 is stored in a processor of a computer. The data acquisition program 400 includes an initial setup segment 410 and a data collection segment 450.

The initial setup segment 410 facilitates the input of the parameters for evaluating the efficacy of drugs. In one preferred embodiment, the initial setup segment 410 includes four main components 412, 414, 416, 418. Each component 412, 414, 416, 418 may include control parameters and/or identification parameters. The initial setup 412 allows for input of control parameters and information parameters regarding overall variables, such as study identification, date, animal environment lights on/off times, and start/stop times. The initial setup 412 may also allow input of control parameters and information parameters pertaining to each animal. The animal treatment setup 414 allows for the input of control parameters and information parameters directed to individual animals, which facilitates tracking of information after completion. Such information may include, for example, an animal's identification number, corresponding scale identification number, and treatment information, such as agent and dose. The pump setup 416 allows for the input of control parameters and information parameters that may include pump identification number corresponding to a particular animal, the syringe diameter, infusion rate, and infusion periods. The scale setup 418 allows for the input of control and information parameters regarding the periodicity of the retrieval of data from the scales associated with the food source of each animal, such as the interval at which data will be collected from each scale, and the control parameters defining the feeding of an animal. Such feeding parameters typically include a change of weight of the food source from one data interval to the next that exceeds a predetermined threshold value. The initial setup segment 410 may be implemented via a graphical user interface on a computer implementing the program 400, such as computer 182 of FIG. 1. So configured, the program 400 implementing the initial setup segment 410 may automatically begin, administer, and conclude the delivery of agents to the animals and the collection of data.

Following the initial setup segment 410, the data acquisition phase 302 controls the delivery of agents and monitoring of the food consumption of the animals. At a predetermined time, the program 400 starts at step 451. The next step 452 switches the pump 160 (FIG. 1) "on" and a dose of the agent is delivered to the animal according to the parameters input during initial setup segment 410. The program 400 then performs the next step 453 and switches to the first cage scale assembly 110 (FIG. 1). The program 400 then performs the step 454 and polls the first scale to collect data, such as the weight of the food source 130 (FIG. 1) associated with a first cage and a first animal. The program compares the current value of the food weight to the previously polled food weight from the same scale and animal, to determine whether the absolute change in food weight exceeds a predetermined threshold value indicative of feeding behavior. If this change in food weight is greater than the predetermined threshold value, the program 400 performs the step 456 of recording the data for later analysis.

The data recording step 456 preferably includes recording information sufficient to identify an animal's feeding patterns. Such information typically includes the animal identification number, the date and time the food weight measurement was taken, the previous food weight, and the current food weight, although it is contemplated that any other information may be included as necessary. Following the data recording step 456, the program 400 performs the step 457 of determining whether the stop time has been reached. If so, then the process is stopped per step 459, and no further data is collected and recorded. Furthermore, agents are no longer delivered to the animals. Similarly, if the change in value in step 455 was less than the predetermined threshold value, the program 400 does not perform step 456 to record data, but instead step 457 is performed to determine whether the stop time has been reached.

If, after performing step 457 and determining that the stop time has not been reached, the program 400 then performs step 458, which switches to the next cage, if any, whereupon the program 400 performs step 454 to poll the next scale weight. The method continues for the second cage just as with the first cage, and the third cage, if any, and so forth. In a preferred embodiment, each cage is polled every twenty seconds, and the program 400 is configured to control the timing of steps 454 to 458 to accomplish regular polling of the cages. When the program 400 has polled each cage, it begins again at step 454 by polling the first cage. This method runs continually until the program 400 has determined that the stop time has been reached in step 457, whereupon the program will stop at step 459.

Figure 5:
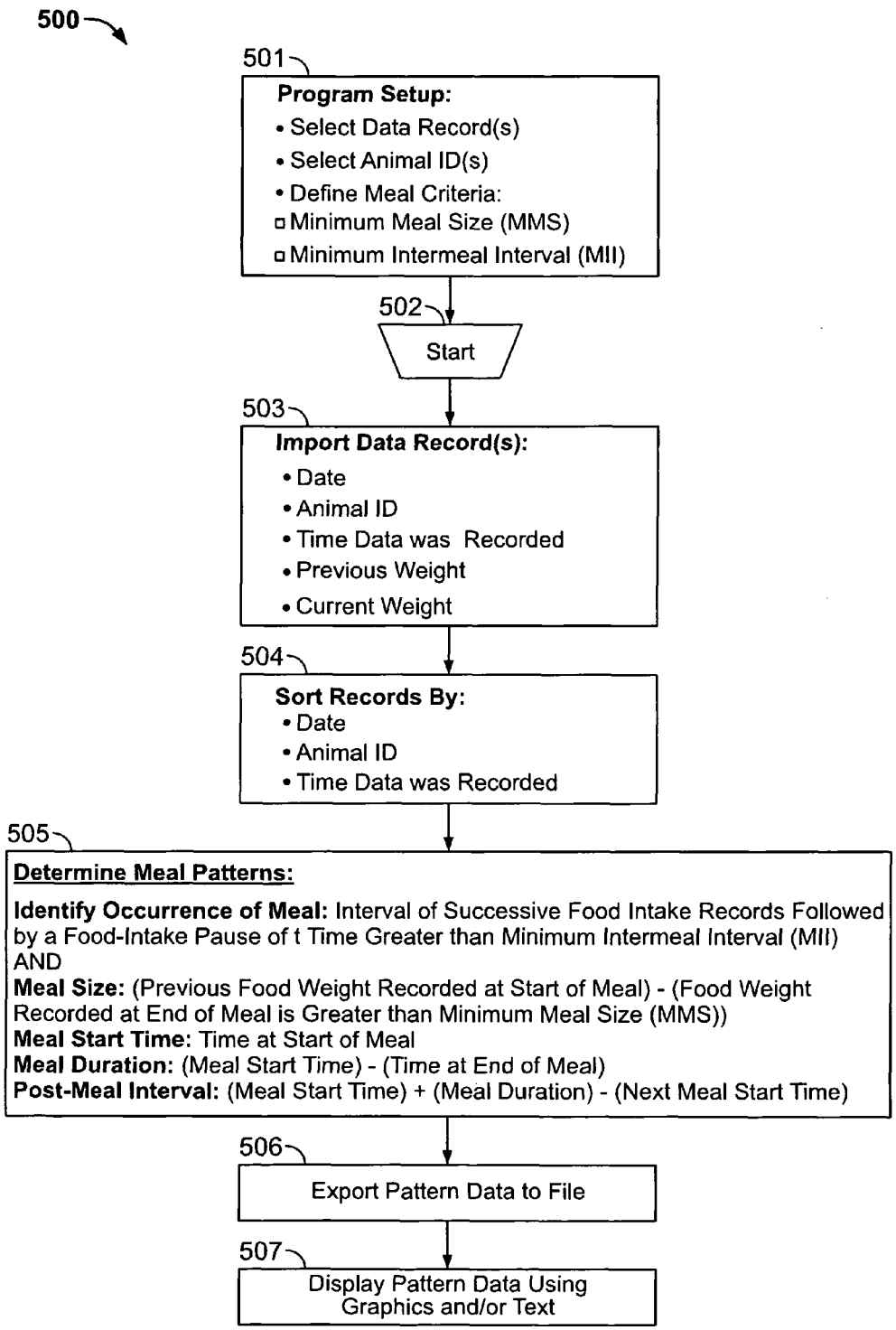
FIG. 5 is a flowchart of an embodiment of the data analyzing phase of FIG. 3 according to the present invention.

FIG. 5 is a flowchart of an embodiment of the data analyzing phase 304 according to the present invention. The data analyzing program 500 analyzes the data collected and recorded by the data collection segment 450 as described with reference to FIG. 4. The data analyzing program 500 is preferably stored in a processor of a computer. The data analyzing program 500 need not necessarily be on the same computer as the software implementing the data acquisition program 400, and may instead be on a separate computer (not shown). In a preferred embodiment, the data analyzing program 500 processes the data collected and recorded by the data management system 300.

The initial step 501 of the data analyzing program 500 includes performing the program setup, which may include, for example, data records to analyze, animal identification data to analyze, and the meal criteria. Defining meal criteria may include defining the minimum meal size in terms of change in food weight, and defining the minimum between-meal interval. The minimum between-meal interval is defined as a predetermined time period of no eating that must be met to define the end of one meal and the start of another. So configured, the data analyzing program 500 may evaluate animal feeding patterns from the data collected throughout a specified duration, which in one preferred embodiment includes data collected at twenty second intervals.

Following the initial setup step 501, the data analyzing program 500 performs the start step 502. After starting, the program 500 performs the step 503 of importing data records stored by the data collection segment 450 of the data acquisition program 400. The data records preferably contain information necessary to identify feeding patterns in the animals being studied, such as the time and date the data was collected, the animal identification data, food weight from previous data acquisition, and food weight from current data acquisition. The latter two data points allow the program 500 to determine food intake, if any, across a series of successive food weight acquisitions for a particular animal.

The program 500 then performs the step 504 of sorting the data records. The data records may be sorted by date, animal identification data, and the time that the data was recorded. Other sorting may also be performed according to predefined criteria, such as the user's preferences.

Once the program 500 has sorted the data records, it may determine feeding patterns according to predetermined parameters, as shown with respect to step 505 in FIG. 5. Examples of feeding pattern data may include identifying the time of occurrence, duration, size and frequency of distinct meals. A meal is defined as an interval of successive food weight data for a specified animal showing a beginning to end difference in food weight that is greater than a predetermined value, the minimum meal size. This interval of successive food weight data must also be preceded and followed by a pause in food weight recording greater than a predetermined value, the minimum between-meal interval. Additional feeding pattern data may include meal start time, meal duration (defined as the absolute value of meal start time minus meal end time for a particular animal), post-meal interval (preferably defined as the absolute value of meal start time plus meal duration minus next meal start time for a particular animal), and average meal size, meal duration and number of meals during specified intervals of time. After one or more feeding patterns have been identified, the program 500 preferably saves the feeding pattern data to a file in the computer's data storage medium per step 506.

Once one or more feeding patterns have been identified, the program 500 may perform the step of displaying the feeding pattern data on, for example, a graphical user interface using graphics and/or text, per step 507. Displaying the feeding pattern data in graphics and/or text allows researchers to quickly identify data trends. In addition, a graphical display of the feeding pattern data allows an instantaneous visualization of the effects of the agent on an animal's feeding patterns, or on average feeding patterns from a group of identically treated animals.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled in the relevant art will realize. Moreover, the various embodiments described above can be combined to provide further embodiments. Accordingly, the invention is not limited by the disclosure, but instead the scope of the invention is to be determined entirely by the following claims.

What is claimed is:

1. A system for determining the efficacy of drugs on an animal, comprising:
    a plurality of cage scale assemblies, each cage scale assembly including a cage, a food source, and a scale, wherein said cage scale assembly is configured to wirelessly send cage scale assembly data to and wirelessly receive the cage scale assembly data from a switchbox;
    said food source available to the animal;
    said scale associated with said food source and in wireless communication with the switchbox;
    said cage scale assembly data consisting of poll date, animal ID, current time, previous scale weight and current scale weight;
    a drug-delivery device in wireless communication with a control unit, the drug-delivery device including a drug source for delivering a predetermined amount of at least one appetite-affecting agent to the animal,
    a control unit configured to:
    store study setup data consisting of study ID, date, lights-on time, lights-off time, experiment start time and experiment stop time,
    store animal treatment setup data consisting of animal ID, cage scale ID, treatments ID, agent(s) and dose(s),
    store pump setup data consisting of pump ID, syringe diameter, infusion rate and infusion periods,
    store scale setup data consisting of polling interval and threshold weight change,
    collect the cage scale assembly data from said switchbox at a predetermined interval,
    determine if the previous scale weight exceeds the current scale weight by an amount greater than the threshold weight change indicating feeding behavior, and if so record the cage scale assembly data, and
    analyze the cage scale assembly data to determine feeding patterns of the animal;
    send instructions to the drug delivery device to stop delivering the predetermined amount of the at least one appetite-affecting agent upon determining that the previous scale weight exceeds the current scale weight by an amount greater than the threshold.

2. The system of claim 1, wherein said appetite-affecting agent is Peptide $YY_{3-36}$.

3. The system of claim 1, wherein said scale is configured to communicate over a network.

4. The system of claim 1, wherein said drug-delivery device is configured to communicate over a network.

5. The system of claim 1, wherein said control unit is configured to communicate over a network.

6. The system of claim 1, wherein said drug-delivery device comprises a plurality of said drug sources.

7. A system for determining the efficacy of drugs on an animal, comprising:
    a plurality of drug-delivery devices, each of said drug-delivery devices including a drug source and a pump, wherein said pump initiates delivery of a predetermined amount of at least one appetite-affecting agent from said drug source to the animal, and said each of said drug-delivery devices is configured to wirelessly send drug-delivery device data to and wirelessly receive the drug-delivery device data from a control unit;
    a plurality of cage scale assemblies, each of said cage scale assemblies including a cage, a scale and a food source, wherein each of said scales are associated with each of said food source for the animal, wherein said each of said cage scale assemblies is configured to wirelessly send cage scale assembly data to and wirelessly receive cage scale assembly data from a switchbox, the cage scale assembly data consisting of poll date, animal ID, current time, previous scale weight and current scale weight;
    a control unit configured to:
    store study setup data consisting of study ID, date, lights-on time, lights-off time, experiment start time and experiment stop time,
    store animal treatment setup data consisting of animal ID, cage scale ID, treatments ID, agent(s) and dose(s),
    store pump setup data consisting of pump ID, syringe diameter, infusion rate and infusion periods,
    store scale setup data consisting of polling interval and threshold weight change,
    wirelessly receive the cage scale assemblies data from the switchbox and wirelessly receive the drug-delivery device data from at least one of said each of said drug-delivery devices at a predetermined interval, and
    determine, for each of said cage scale assemblies, if the previous scale weight exceeds the current scale weight by greater than the threshold weight change and if so, store the cage scale assembly data and the drug-delivery device data,
    send instructions to the drug delivery device to stop delivering the predetermined amount of the at least one appetite-affecting agent upon determining that the previous scale weight exceeds the current scale weight by an amount greater than the threshold.

8. The system of claim 7, wherein said each of said scales is configured to determine food weight and transmit food weight data to a processor.

9. The system of claim 7, wherein a storage medium is operatively associated with said control unit.

10. The system of claim 7, wherein said appetite-affecting agent is at least one from the following group of: Peptide $YY_{3-36}$ (PYY), cholecystokinin, amylin, salmon calcitonin, glucagon-like peptide-1 (GLP-1), exendin-4, oxyntomodulin, pancreatic polypeptide, gastrin-releasing peptides GRP-27 and GRP-10, enterostatin, apolipoprotein A-IV, leptin, melanocortin receptor 3 and 4 agonists including melanotan II, opioid receptor antagonists including naloxone and naltrexone, and endocanabinoid receptor antagonists AM251 and Rimonabant.

11. A method of determining the efficacy of a drug, the method comprising:
    providing a plurality of drug-delivery devices, each of the drug-delivery devices being capable of delivering a predetermined amount of at least one appetite-affecting agent to an animal of a plurality of animals, at least one of the drug-delivery devices being connected to one of the plurality of animals;

providing a control unit configured to:
store study setup data consisting of study ID, date, lights-on time, lights-off time, experiment start time and experiment stop time,
store animal treatment setup data consisting of animal ID, cage scale ID, treatments ID, agent(s) and dose(s),
store pump setup data consisting of pump ID, syringe diameter, infusion rate and infusion periods, and
store scale setup data consisting of a polling interval and a threshold weight change indicating feeding behavior,
administering the at least one appetite-affecting agent to the one of the plurality of animals;
supplying at least one food source available to one of the plurality of animals;
arranging a plurality of scales, at least one of the plurality of scales being in association with the at least one food source, wherein the plurality of scales are in wireless communication with a switchbox;
monitoring food consumption of the animals of the plurality of animals;
determining if the previous scale weight exceeds the current scale weight by greater than the threshold weight change and if so, recording scale data consisting of poll date, animal ID, current time, previous scale weight and current scale weight via the switchbox;
gathering drug-delivery device data wirelessly sent from at least one of the plurality of drug-delivery devices to the control unit, wherein the drug-delivery device data includes an identification number of the animal, a date of the at least one appetite-affecting agent delivered to the animal, a type of the at least one appetite-affecting agent delivered to the animal, a dose of the at least one appetite-affecting agent delivered to the animal, an infusion rate of the at least one appetite-affecting agent delivered to the animal, and at least one time interval of delivery of the at least one appetite-affecting agent delivered to the animal; and
evaluating the scale data and the drug-delivery device data to obtain feeding patterns of the animals of the plurality of animals with respect to the at least one appetite-affecting agent
stopping delivery of the at least one appetite-affecting agent upon determining that the previous scale weight exceeds the current scale weight by greater than the threshold weight change.

\* \* \* \* \*